US00PP19214P2

(12) United States Plant Patent
Thapnarin

(10) Patent No.: US PP19,214 P2
(45) Date of Patent: Sep. 9, 2008

(54) ***PHILODENDRON* PLANT NAMED 'TWYPH0007'**

(50) Latin Name: *Philodendron selloum*
Varietal Denomination: TWYPH0007

(75) Inventor: Wongchan Thapnarin, Umphure Bangyai Nonthaburi (TH)

(73) Assignee: Kerry's Bromeliads, Inc., Apopka, FL (US)

( * ) Notice: Subject to any disclaimer, the term of this patent is extended or adjusted under 35 U.S.C. 154(b) by 0 days.

(21) Appl. No.: 11/803,223

(22) Filed: May 14, 2007

(51) Int. Cl.
*A01H 5/00* (2006.01)

(52) U.S. Cl. ..... Plt./381

(58) Field of Classification Search ..... Plt./381
See application file for complete search history.

*Primary Examiner*—S. B. McCormick Ewoldt
(74) *Attorney, Agent, or Firm*—Jondle & Associates, P.C.

(57) ABSTRACT

A new *Philodendron* plant particularly distinguished by yellowish-green to green and dense foliage, a compact growth habit and ovate to narrow-ovate shaped foliage with pinnatifid margins and deep lobes, is disclosed.

3 Drawing Sheets

Genus and species: *Philodendron selloum.*
Variety denomination: 'TWYPH0007'.

BACKGROUND OF THE NEW PLANT

The present invention comprises a new and distinct cultivar of *philodendron* plant, botanically known as *Philodendron selloum,* and hereinafter referred to by the cultivar name 'TWYPH0007'. The new cultivar is the result of a somaclonal variant of *Philodendron selloum* 'Winterbourn' (U.S. Plant Pat. No. 7,030) from approximately 10,000 micropropagated plants of the original cultivar in 1999 in Nonthaburi, Thailand.

The new cultivar was created in 1999 in Nonthaburi, Thailand and has been asexually reproduced repeatedly by micropropagation and division in Nonthaburi, Thailand over an eight-year period. 'TWYPH0007' has not been observed under all possible environmental conditions. The present invention has been found to retain its distinctive characteristics through successive asexual propagations.

SUMMARY OF THE INVENTION

The following are the most outstanding and distinguishing characteristics of this new cultivar when grown under normal horticultural practices in Nonthaburi, Thailand.

1. Yellowish-green to green-colored and dense foliage;
2. A compact growth habit; and
3. Ovate to narrow-ovate shaped foliage with pinnatifid margins and deep lobes.

DESCRIPTION OF THE PHOTOGRAPHS

This new *philodendron* plant is illustrated by the accompanying photographs which show the overall plant habit and the immature and mature foliage of the plant; the colors shown are as true as can be reasonably obtained by conventional photographic procedures. The photographs are of a 7-year-old plant with immature and mature foliage grown under 50% shade conditions outdoors in Nonthaburi, Thailand.

DESCRIPTION OF THE NEW CULTIVAR

Figure 1:
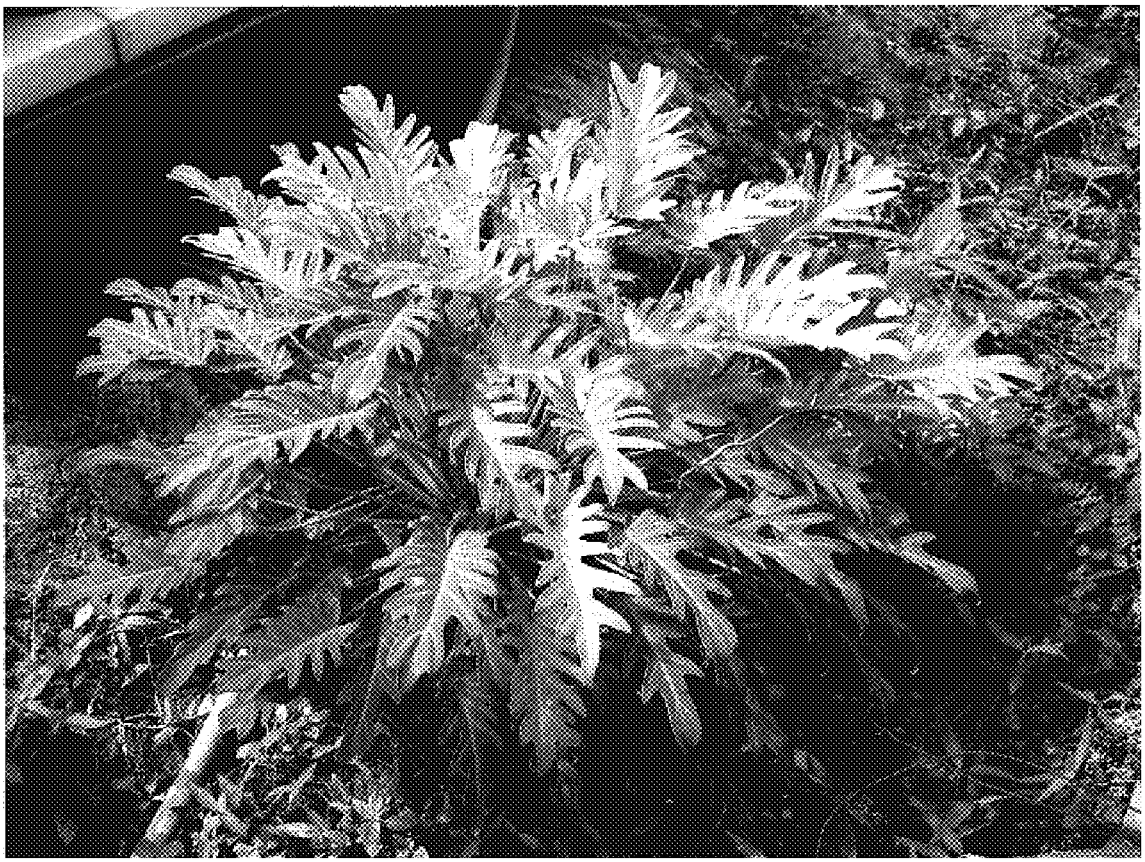
FIG. 1 shows the overall plant habit.
Figure 2:
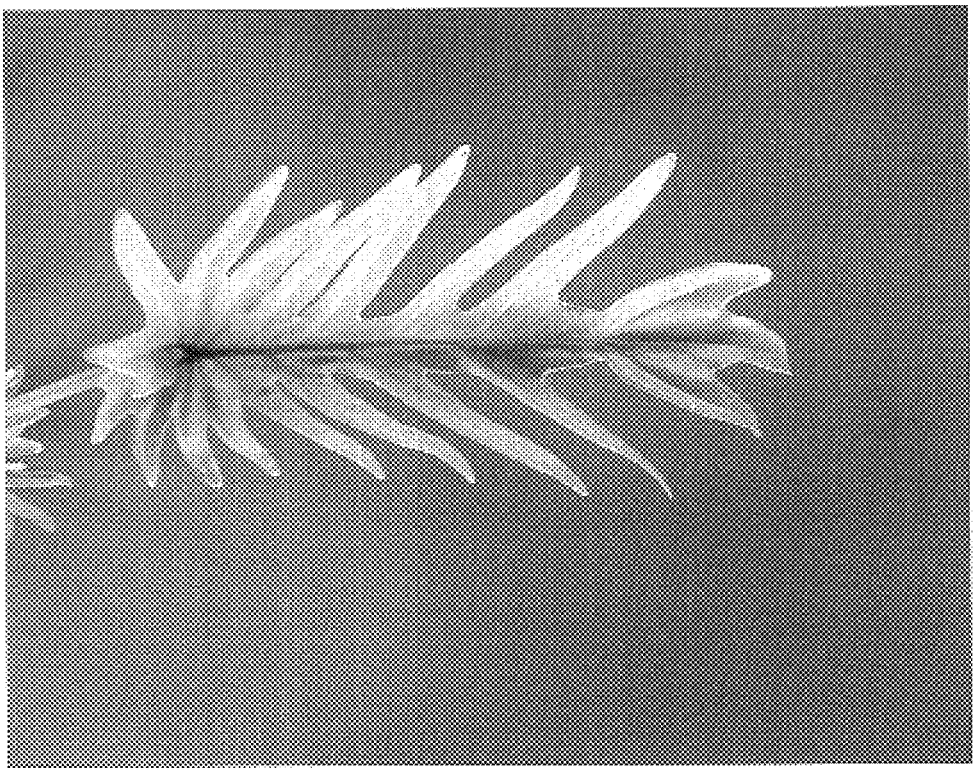
FIG. 2 shows the upper surface of an immature leaf.
Figure 3:
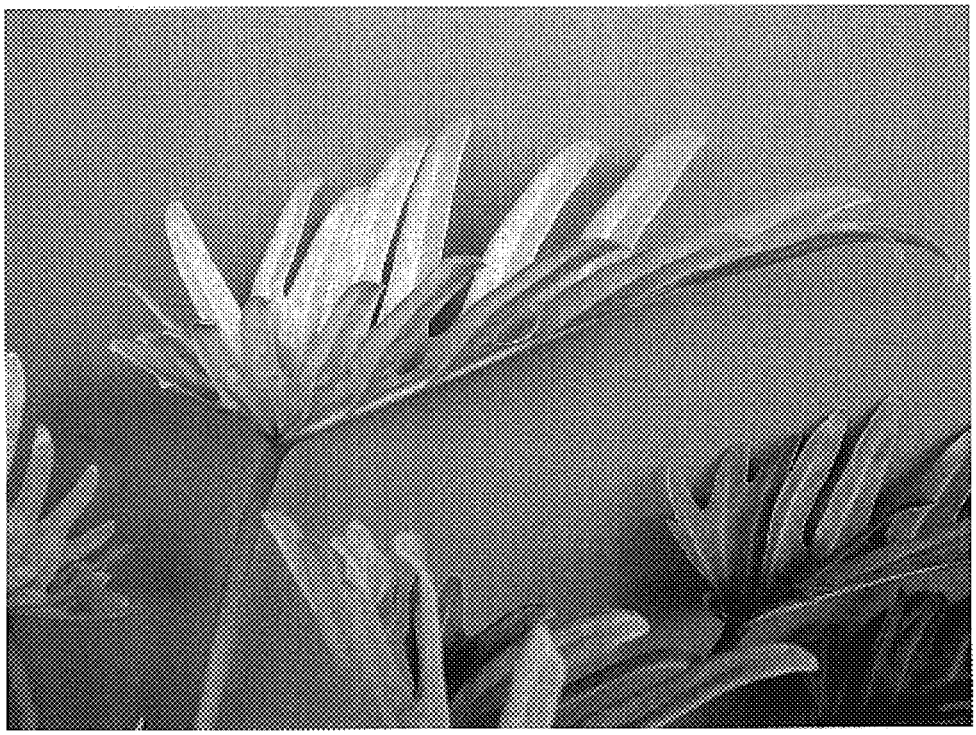
FIG. 3 shows the lower surface of an immature leaf.
Figure 4:
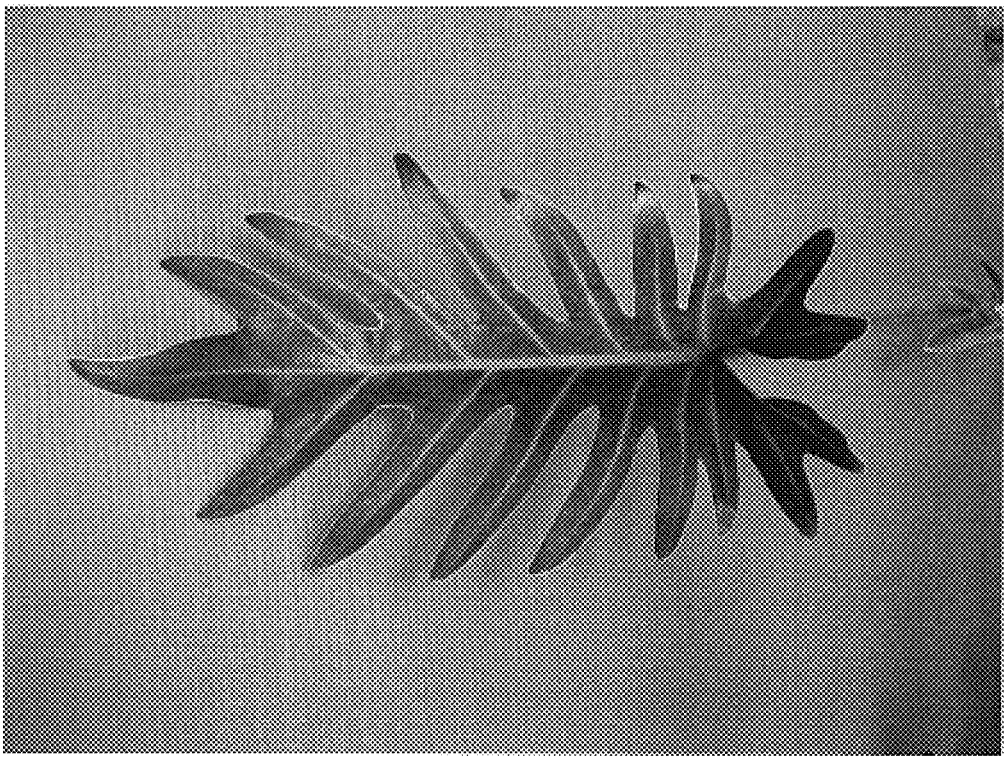
FIG. 4 shows the upper surface of a mature leaf.
Figure 5:
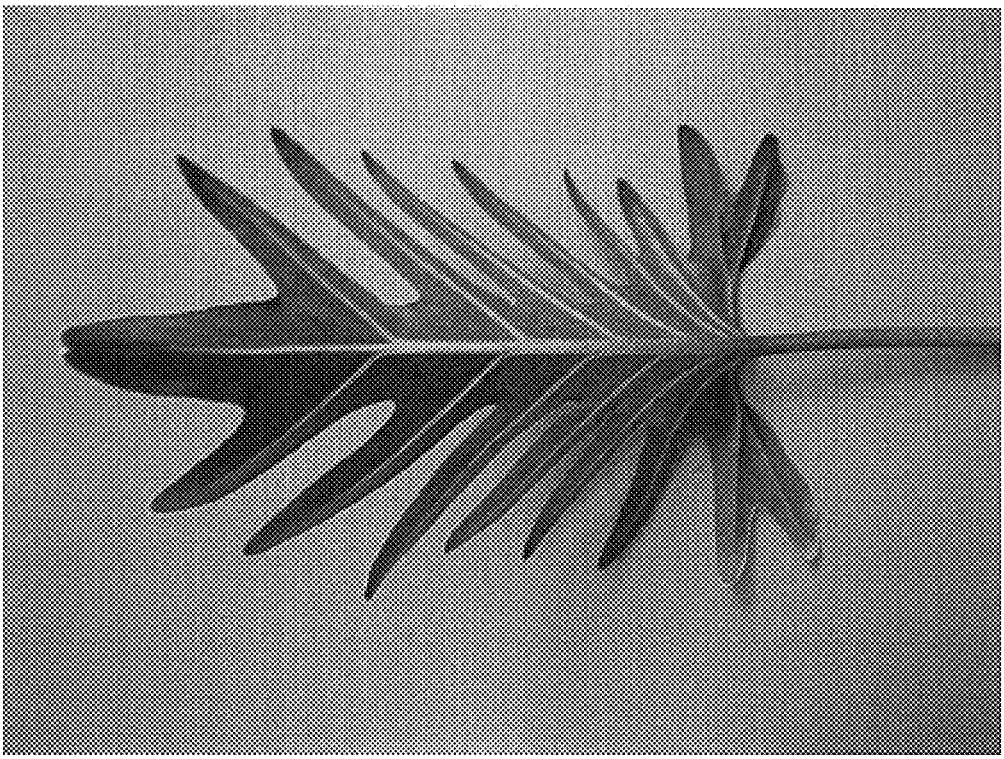
FIG. 5 shows the lower surface of a mature leaf.

The following detailed descriptions set forth the distinctive characteristics of 'TWYPH0007'. The data which define these characteristics were collected from asexual reproductions carried out in Nonthaburi, Thailand. The plant history was taken on 7-year-old plants having two suckers and grown under 50% shade conditions in Nonthaburi, Thailand. Color readings were taken under natural light. Color references are primarily to the R.H.S. Colour Chart of The Royal Horticultural Society of London (R.H.S.) (2001).

DETAILED BOTANICAL DESCRIPTION OF THE NEW PLANT

Classification:
- *Family.*—Araceae.
- *Botanical.*—*Philodendron selloum.*
- *Common name.*—Split leaf or tree *philodendron.*

Parentage: A somaclonal variant of *Philodendron selloum* 'Winterbourn' (U.S. Plant Pat. No. 7,030).

Growth:
- *Growth and branching habit.*—Upright and rarely branched; leaves form a dense head; stems have very short internodes with leaf scars that are crowded together.
- *Height (from soil line to the top).*—70 cm to 90 cm.
- *Width.*—90 cm to 110 cm.

Stem:
- *Average number per plant.*—1.
- *Diameter (for a 7-year-old plant).*—3.0 cm to 3.5 cm.
- *Internode length.*—1.5 cm to 3 cm.
- *Color.*—Approximately RHS 200C; leaf scar is approximately RHS 196A.

Leaves:
- *Size.*—Length: 22 cm to 35 cm. Width: 12 cm to 20 cm.
- *Shape.*—Ovate to narrow-ovate.
- *Apex.*—Acuminate.

*Base.*—Truncate.

*Margin.*—Slightly recurved pinnatifid margin with 5 to 8 pairs of lobes.

*Aspect.*—Alternate arrays.

*Lobes.*—Side lobes taper on immature leaves; as leaves mature, the side lobes are nearly parallel and slightly curved towards the terminal lobe; the terminal lobe is poorly separated from the adjacent lobes; the lobes are pointed about 50 degrees forward; the lobes are obtuse to acute.

*Venation pattern.*—Primary veins are sub-opposite to alternate.

*Color* (*immature leaves*).—Upper surface: RHS 150B. Lower surface: RHS 150C.

*Color* (*mature leaves*).—Upper surface: RHS 139B. Lower surface: RHS 141C.

*Texture* (*both immature and mature*).—Smooth and glabrous.

*Appearance* (*both immature and mature*).—Glossy.

*Venation and midrib color* (*immature leaves*).—Upper surface: RHS 150B. Lower surface: RHS 179D, with the midrib-petiole joint flushed with RHS 171C.

*Venation color* (*mature leaves*).—Upper surface: RHS 141C. Lower surface: RHS 139D with the midrib-petiole joint flushed with RHS 183C.

*Petiole* (*from fourth expanded leaf from the apex*).—Aspect: Straight, about 30 degrees to 40 degrees from the vertical axis. Length: 35 cm to 40 cm. Diameter (mid-section): 0.5 cm to 0.7 cm. Immature color: RHS 154B and proximal end near RHS 171C. Mature color: RHS 144B and proximal end near RHS 183C. Texture: Smooth.

Inflorescence: None observed.

Reproductive organs: None observed.

Fruit and seed set: No seed set observed so far.

Disease and insect resistance: No particular resistance or susceptibility has been observed.

COMPARISON WITH PARENTAL AND COMMERCIAL CULTIVARS

'TWYPH0007' differs from the parental cultivar 'Winterbourn' (U.S. Plant Pat. No. 7,030) in that 'TWYPH0007' has yellowish-green to green foliage, while 'Winterbourn' has green foliage. Additionally, the growth rate of 'TWYPH0007' is approximately 10% to 15% lower than that of 'Winterbourn'.

'TWYPH0007' differs from the commercial cultivar 'Pastel Sport #2' (U.S. Plant Pat. No. 16,123) in that 'TWYPH0007' has immature leaves which are yellowish-green with light greyed-red venation, while 'Pastel Sport #2' has immature leaves that are yellow-orange with pink venation. Additionally, 'TWYPH0007' has a longer internode length (1.5 cm to 3 cm) and leaves that have an acumiate apex and truncate base, while 'Pastel Sport #2' has a shorter internode (0.5 cm to 1.0 cm) and leaves that have an acute apex and hastate base.

I claim:

1. A new and distinct cultivar of *Philodendron* plant as shown and described herein.

* * * * *